United States Patent
Izawa et al.

(10) Patent No.: US 10,144,687 B2
(45) Date of Patent: Dec. 4, 2018

(54) METHOD FOR PRODUCING 1,4-BUTANEDIOL

(71) Applicant: MITSUBISHI CHEMICAL CORPORATION, Chiyoda-ku (JP)

(72) Inventors: Yusuke Izawa, Mie (JP); Masaru Utsunomiya, Tokyo (JP); Kouta Tanaka, Mie (JP); Norikazu Konishi, Mie (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 483 days.

(21) Appl. No.: 14/147,885

(22) Filed: Jan. 6, 2014

(65) Prior Publication Data

US 2014/0116872 A1   May 1, 2014

Related U.S. Application Data

(63) Continuation of application No. PCT/JP2012/067011, filed on Jul. 3, 2012.

(30) Foreign Application Priority Data

Jul. 4, 2011 (JP) ................. 2011-148328

(51) Int. Cl.
  *C07C 29/80* (2006.01)
  *C07C 29/88* (2006.01)

(52) U.S. Cl.
  CPC .............. *C07C 29/80* (2013.01); *C07C 29/88* (2013.01)

(58) Field of Classification Search
  USPC ................... 585/28–38; 203/28–38
  See application file for complete search history.

(56) References Cited

U.S. PATENT DOCUMENTS

| | | | |
|---|---|---|---|
| 4,213,000 A | 7/1980 | Coates | |
| 4,465,873 A * | 8/1984 | Harano | C07C 29/141 568/862 |
| 4,511,708 A | 4/1985 | Kasuga et al. | |
| 6,137,016 A * | 10/2000 | Wood | C07C 29/88 568/868 |
| 6,387,224 B1 * | 5/2002 | Pinkos | C07C 29/80 203/33 |
| 2006/0122365 A1 | 6/2006 | Pinkos et al. | |
| 2007/0260073 A1 | 11/2007 | Wood et al. | |
| 2008/0058541 A1 * | 3/2008 | Bowen | C07F 7/20 556/413 |
| 2009/0099392 A1 | 4/2009 | Hino et al. | |
| 2009/0171037 A1 | 7/2009 | Aoshima et al. | |

FOREIGN PATENT DOCUMENTS

| | | |
|---|---|---|
| JP | 59-140223 A | 8/1984 |
| JP | 61-197534 | 9/1986 |
| JP | 2-167274 A | 6/1990 |
| JP | 06-239778 | 8/1994 |
| JP | 07-082187 | 3/1995 |
| JP | 7-118253 A | 5/1995 |
| JP | 10-265418 | 10/1998 |
| JP | 2000-507566 A | 6/2000 |
| JP | 2003-26622 A | 1/2003 |
| JP | 2004-107619 | 4/2004 |
| JP | 2006-503050 A | 1/2006 |
| JP | 2008-101143 A | 5/2008 |
| JP | 2008-514684 | 5/2008 |
| WO | WO 97/36846 A1 | 10/1997 |
| WO | WO 2007/125909 A1 | 11/2007 |

OTHER PUBLICATIONS

Office Action dated Feb. 23, 2016 in Japanese Patent Application No. 2012-149684 (with English language translation).
U.S. Appl. No. 14/560,714, filed Dec. 4, 2014, Utsunomiya, et al.
Notification of Reasons for Refusal dated Dec. 8, 2015 in Japanese Patent Application No. 2012-149938 (with unedited computer generated English translation).
U.S. Appl. No. 14/150,174, filed Jan. 8, 2014, Izawa, et al.
International Search Report dated Oct. 2, 2012 in PCT/JP2012/067011 filed Jul. 3, 2012.
Office Action dated Jul. 19, 2016 in Japanese Patent Application No. 2012-149938 (with unedited computer generated English translation).

* cited by examiner

*Primary Examiner* — In Suk C Bullock
*Assistant Examiner* — Ali Z Fadhel
(74) *Attorney, Agent, or Firm* — Oblon, McClelland, Maier & Neustadt, L.L.P.

(57) ABSTRACT

An object of the present invention is to provide an industrially advantageous production method of 1,4BG, ensuring that generation of THF in the crude 1,4BG can be also suppressed and at the same time, the concentration of 2-(4-hydroxybutoxy)-tetrahydrofuran can be reduced. The present invention relates to a method for producing 1,4-butanediol, comprising heating crude 1,4-butanediol containing from 0.01 to 0.5 wt % of 2-(4-hydroxybutoxy)-tetrahydrofuran and from 1 to 25 wt % of water at 80° C. or more in the presence of an amine to obtain purified 1,4-butanediol.

16 Claims, No Drawings

METHOD FOR PRODUCING 1,4-BUTANEDIOL

CROSS-REFERENCE TO RELATED APPLICATIONS

This application is a Continuation of PCT/JP2012/067011, which was filed on Jul. 3, 2012. This application is based upon and claims the benefit of priority to Japanese Application No. 2011-148328, which was filed on Jul. 4, 2011, the entire contents of which are incorporated herein by reference.

TECHNICAL FIELD

The present invention relates to a method for producing 1,4-butanediol. More specifically, the present invention relates to a method for producing 1,4-butanediol to obtain purified 1,4-butanediol by reducing the 2-(4-hydroxybutoxy)-tetrahydrofuran concentration in crude 1,4-butanediol containing 2-(4-hydroxybutoxy)-terahydrofuran.

BACKGROUND ART 1,4-Butanediol (hereinafter, sometimes simply referred to as "1,4BG") is a raw material of tetrahydrofuran (hereinafter, sometimes simply referred to as "THF") used as a solvent and is a substance useful also as a raw material of a polyester material such as polybutylene terephthalate (hereinafter, sometimes simply referred to as "PBT").

Conventionally, a method for industrially producing 1,4BG is known. For example, there are known a method for producing 1,4BG by hydrogenation and hydrolysis of 1,4-diacetoxy-2-butene that is obtained by diacetoxylation of butadiene, a method for obtaining a 1,4BG-containing crude hydrogenation product by using maleic anhydride as a raw material and hydrogenating it, a method for producing 1,4BG by hydrogenating butynediol that is obtained by using acetylene as a raw material and contacting it with an aqueous formaldehyde solution, a method for obtaining 1,4BG through oxidation of propylene, a method of hydrogenating succinic acid obtained by a fermentation process, and a method for direct production from sugar by a fermentation process.

The thus-obtained crude 1,4BG sometimes contains 2-(4-hydroxybutoxy)-tetrahydrofuran as an impurity, and removal of this substance by distillation is difficult, because its boiling point is close to that of 1,4BG. Patent Document 1 describes a method of decomposing 2-(4-hydroxybutoxy)-tetrahydrofuran in the crude 1,4BG by using various platinum element-supported catalysts so as to reduce the substance. Patent Document 2 reveals the fact that in a continuous process for producing 1,4BG by hydrogenation and hydrolysis of 1,4-diacetoxy-2-butene obtained by diacetoxylation of butadiene, a hydrogenation catalyst powder inflows in the distillation step to cause production of 2-(4-hydroxybutoxy)-tetrahydrofuran in 1,4BG in a distillation column and when PBT is produced using thus obtained 1,4BG, PBT is colored. Patent Document 3 describes a method where the temperature and pressure inside an esterification reaction tank and a distillation column for producing PBT are appropriately controlled to decompose 2-(4-hydroxybutoxy)-tetrahydrofuran under acidic conditions so as to achieve conversion to 2,3-dihydrofuran, 2-hydroxytetrahydrofuran and the like and these substances are removed together with water, THF and the like by the distillation column from the esterification reaction tank.

BACKGROUND ART DOCUMENT

Patent Document

Patent Document 1: JP-A-61-197534 (the term "JP-A" as used herein means an "unexamined published Japanese patent application")
Patent Document 2: JP-A-10-265418
Patent Document 3: JP-A-2004-107619

SUMMARY OF INVENTION

Problem that Invention is to Solve

Crude 1,4BG may allow generation of THF under acidic conditions to cause a loss of raw material 1,4BG in the PBT production and a rise in the differential pressure inside a distillation column. In particular, crude 1,4BG containing not only 2-(4-hydroxybutoxy)-tetrahydrofuran but also water has a problem that at the time of producing a polyester such as PBT, a byproduct or a solid compound occurs to inhibit the continuous production and as a result, the productivity deteriorates.

The present invention has been made by taking into account these problems, and an object of the present invention is to provide an industrially advantageous production method of 1,4BG, ensuring that when suppressing generation of 2-(4-hydroxybutoxy)-tetrahydrofuran from crude 1,4BG, generation of THF in the crude 1,4BG can be also suppressed and at the same time, the concentration of 2-(4-hydroxybutoxy)-tetrahydrofuran can be reduced.

Means for Solving Problem

As a result of intensive studies to solve the above-described problem, the present inventors have accomplished the present invention by finding that when crude 1,4BG containing from 0.01 to 0.5 wt % of 2-(4-hydroxybutoxy)-tetrahydrofuran and from 1 to 25 wt % of water is heated at 80° C. or more in the presence of an amine or crude 1,4-butanediol containing from 0.01 to 0.5 wt % of 2-(4-hydroxybutoxy)-tetrahydrofuran is heated at 80° C. or more in the presence of an amine and water in an amount of 1 to 25 wt % based on the crude 1,4-butanediol, the concentration of 2-(4-hydroxybutoxy)-tetrahydrofuran can be reduced.

The present invention has been achieved based on the finding above, and the gist of the present invention resides in the following (1) to (6).

(1) A method for producing 1,4-butanediol, comprising heating crude 1,4-butanediol containing from 0.01 to 0.5 wt % of 2-(4-hydroxybutoxy)-tetrahydrofuran and from 1 to 25 wt % of water at 80° C. or more in the presence of an amine to obtain purified 1,4-butanediol.

(2) A method for producing 1,4-butanediol, comprising heating crude 1,4-butanediol containing from 0.01 to 0.5 wt % of 2-(4-hydroxybutoxy)-tetrahydrofuran at 80° C. or more in the presence of an amine and water in an amount of 1 to 25 wt % based on said crude 1,4-butanediol to obtain purified 1,4-butanediol.

(3) The method for producing 1,4-butanediol described in the above (1) or (2), wherein pH of said crude 1,4-butanediol is 7 or more.

(4) The method for producing 1,4-butanediol described in any one of the above (1) to (3), wherein the amount of said amine is from 1 ppm by weight to 1 wt % based on the crude 1,4-butanediol.
(5) The method for producing 1,4-butanediol described in any one of the above (1) to (4), wherein said crude 1,4-butanediol is heated at 80° C. or more in a distillation column.
(6) The method for producing 1,4-butanediol described in any one of the above (1) to (5), further comprising a step of distilling purified 1,4-butanediol obtained by heating said crude 1,4-butanediol at 80° C. or more.

Advantageous Effects of Invention

According to the present invention, impurities contained in crude 1,4-butanediol can be efficiently reduced.

MODE FOR CARRYING OUT INVENTION

The present invention is described in detail below. Here, "wt %" and "ppm by weight" have the same meanings as "mass %" and "ppm by mass", respectively.

The crude 1,4BG used in the present invention can be obtained by a known method. For example, 1,4-butanediol obtained by hydrogenation and hydrolysis of 1,4-diacetoxy-2-butene that is obtained by diacetoxylation of butadiene can be used. Alternatively, for example, 1,4-butanediol obtained by hydrogenation of maleic anhydride, 1,4-butanediol derived from acetylene by the Reppe process, 1,4-butanediol obtained through oxidation of propylene, 1,4-butanediol obtained by hydrogenating succinic acid that is obtained by a fermentation process, and 1,4-butanediol produced directly from sugar by a fermentation process can be used. In these production methods of 1,4-butanediol, 2-(4-hydroxybutoxy)-tetrahydrofuran occurs as a byproduct. Incidentally, in the case of, for example, the 1,4-butanediol obtained by performing hydrogenation and hydrolysis of 1,4-diacetoxy-2-butene that is obtained by diacetoxylation of butadiene, the 1,4-butanediol obtained through oxidation of propylene, the 1,4-butanediol obtained by hydrogenating succinic acid that is obtained by a fermentation process, and the 1,4-butanediol produced directly from sugar by a fermentation process, a solution withdrawn from the production process may be used as it is. Also, the crude 1,4BG obtained by those methods may be used after decreasing or increasing the amount of 2-(4-hydroxybutoxy)-tetrahydrofuran or water contained therein according to another purpose. The 1,4-butanediol derived from acetylene by the Reppe process may be used as the crude 1,4BG of the present invention by adding water thereto.

The crude 1,4BG of the present invention may contain various byproducts occurring in those known production methods, such as 1-acetoxy-4-hydroxybutane, dehydrated dimer or dehydrated trimer of 1,4-butanediol, and gamma butyrolactone.

In the present invention, the crude 1,4-butanediol allows water to exist therein at a concentration of 1 to 25 wt %, preferably from 2 to 20 wt %, more preferably from 5 to 16 wt %. If the water concentration is too high, the production cost may be increased due to rise in the energy cost or reduction in the reaction rate during production of a polyester or tetrahydrofuran. On the other hand, if the water concentration is too small, the effects of the present invention tend to decrease.

In the present invention, the crude 1,4-butanediol contains 2-(4-hydroxybutoxy)-tetrahydrofuran at a concentration of 0.01 to 0.5 wt %, preferably from 0.02 to 0.4 wt %, more preferably from 0.03 to 0.3 wt %. If the 2-(4-hydroxybutoxy)-tetrahydrofuran concentration is too high, the load for obtaining the effects of the present invention may be increased to cause a rise in the production cost, whereas if the 2-(4-hydroxybutoxy)-tetrahydrofuran concentration is too small, the effects of the present invention tend to decrease.

In the present invention, the above-described crude 1,4BG must be heated at 80° C. or more. In the present invention, the method for heating is not particularly limited, but heating can be performed by a distillation column, an extraction tank, a pipe, a heat exchanger or the like. The heating temperature is usually 80° C. or more, preferably from 100 to 250° C., more preferably from 120 to 200° C. The heating time is arbitrarily set but is usually from 1 minute to 100 hours, preferably from 5 minutes to 10 hours.

By virtue of performing the heating operation of the present invention, at the time of producing a polyester or tetrahydrofuran by using 1,4BG as a raw material, the content of 2-(4-hydroxybutoxy)-tetrahydrofuran which leads to a byproduced solid product can be reduced before introduction into a reactor for the production of a polyester or tetrahydrofuran, and more stable operation can be realized. Incidentally, 2-(4-hydroxybutoxy)-tetrahydrofuran whose content is reduced by the operation above is partially converted to 2-hydroxytetrahydrofuran and can be easily separated from 1,4-butanediol or tetrahydrofuran in the purification step.

Also, in the present invention, the crude 1,4BG is heated at 80° C. or more in the presence of an amine. The method for making an amine to exist in the crude 1,4BG is not particularly limited but, for example, a method of mixing the crude 1,4BG and an amine-based compound represented by the following formula (1), and a method of bringing the crude 1,4BG into contact with an anion exchange resin and eluting an amine component contained in the anion exchange resin into the crude 1,4BG, are preferred.

[Chem. 1]

(1)

In formula (1), each of $R^1$ to $R^3$ is preferably independently a hydrogen atom, an alkyl group, an aryl group or an amino group. These groups may further have a substituent, and the substituent may contain a heteroatom. In addition, $R^1$ to $R^3$ may be the same as or different from each other but a case where all of $R^1$ to $R^3$ are a hydrogen atom is excluded.

The alkyl group is a chain (linear or branched) alkyl group or a cyclic alkyl group. The chain alkyl group is usually an alkyl group having a carbon number of 1 to 20, preferably from 1 to 12, and specific examples thereof include a methyl group, an ethyl group, an n-propyl group, an i-propyl group, an n-butyl group, an i-butyl group, a sec-butyl group, a tert-butyl group, a pentyl group, a hexyl group, an octyl group, and a decyl group. The cyclic alkyl group is usually an alkyl group having a carbon number of 3 to 20, preferably from 4 to 11, and specific examples thereof include a cyclopentyl group, a cyclohexyl group, an a cyclooctyl group. The substituent which may be substituted on the alkyl group is not particularly limited as long as it does not seriously inhibit the effects of the present invention, but examples thereof include an aryl group, an acyl group, a hydroxy group, an alkoxy group, an aryloxy group, an alkylaryloxy group, an amino group, an aminoalkyl group, and a sulfide group, and a substituent having a molecular weight of about 200 or less is usually used. Also, the substituent may contain a heteroatom such as oxygen, nitrogen, sulfur and phosphorus.

Examples of the aryl group include a phenyl group, a benzyl group, a mesityl group, a naphthyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 2-ethylphenyl group, an isoxazolyl group, an isothiazolyl group, an imidazolyl group, an oxazolyl group, a thiazolyl group, a thiadiazolyl group, a thienyl group, a thiophenyl group, a triazolyl group, a tetrazolyl group, a pyridyl group, a pyrazinyl group, a pyrimidinyl group, a pyridazinyl group, a pyrazolyl group, a pyrrolyl group, a pyranyl group, a furyl group, a furazanyl group, an imidazolidinyl group, an isoquinolyl group, an isoindolyl group, an indolyl group, a quinolyl group, a pyridothiazolyl group, a benzimidazolyl group, a benzoxazolyl group, a benzothiazolyl group, a benzotriazolyl group, a benzofuranyl group, an imidazopyridinyl group, a triazopyridinyl group, an a purinyl group and the like. The aryl group has a carbon number of usually from 5 to 20, preferably from 5 to 12, and encompasses a heteroaryl group containing oxygen, nitrogen, sulfur or the like. The substituent which may be substituted on the aryl group is not particularly limited as long as it does not seriously inhibit the effects of the present invention, but examples thereof include an alkyl group having a carbon number of 1 to 10, an acyl group having a carbon number of 1 to 10, an alkoxy group having a carbon number of 1 to 10, a cycloalkyl group having a carbon number of 1 to 10, an aryl group having a carbon number of 6 to 10, an aryloxy group having a carbon number of 6 to 10, an alkylaryl group having a carbon number of 7 to 12, an alkylaryloxy group having a carbon number of 7 to 12, an arylalkyl group having a carbon number of 7 to 12, an arylalkoxy group having a carbon number of 7 to 12, and a hydroxy group. Also, the substituent may contain a heteroatom such as oxygen, nitrogen, sulfur, phosphorus and halongen.

Specific examples include a phenyl group, a benzyl group, a mesityl group, a naphthyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 2-ethylphenyl group, a 2-isopropylphenyl group, a 2-tert-butylphenyl group, a 2,4-di-tert-butylphenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 3,4-dichlorophenyl group, a 3,5-dichlorophenyl group, a 4-trifluoromethylphenyl group, a 2-methoxyphenyl group, a 3-methoxyphenyl group, a 4-methoxyphenyl group, a 3,5-dimethoxyphenyl group, a 4-cyanophenyl group, a 4-nitrophenyl group, a 4-aminophenyl group, a trifluoromethylphenyl group, and a pentafluorophenyl group.

The amino group has a carbon number of usually from 0 to 20, preferably from 0 to 12. Specific examples thereof include a methylamino group, an ethylamino group, a propylamino group, a butylamino group, a dimethylamino group, a diethylamino group, an anilino group, a toluidino group, an anisidino group, a diphenylamino group, and an N-methyl-N-phenylamino group. The substituent which may be substituted on the amino group is not particularly limited as long as it does not seriously inhibit the effects of the present invention, but examples thereof include an aryl group, an acyl group, a hydroxy group, an alkoxy group, an aryloxy group, an alkylaryloxy group, an amino group, an aminoalkyl group, and a sulfide group, and a substituent having a molecular weight of about 200 or less is usually used. Also, the substituent may contain a heteroatom such as oxygen, nitrogen, sulfur and phosphorus.

In addition, $R^1$ and $R^2$, $R^2$ and $R^3$, and $R^3$ and $R^1$ may combine with each other to form a ring, respectively.

Incidentally, in the case of mixing the crude 1,4BG and an amine-based compound represented by formula (1), the existence form of an amine in the crude 1,4BG may be the mixed compound itself or may be an amine decomposed from the mixed amine-based compound represented by formula (1).

In the case of eluting an amine component contained in an anion exchange resin into the crude 1,4BG, the crude 1,4BG is brought into contact with the anion exchange resin, and the contact form is not particularly limited. Examples include a method of adding an anionic exchange resin to the crude 1,4BG to elute an amine, and a method of flowing the crude 1,4BG through a vessel, pipe or the like filled with an anion exchange resin to elute an amine. Among others, from the standpoint that a step of heating the crude 1,4BG or separating the anion exchange resin after heating can be omitted, it is preferred to elute an amine by flowing the crude 1,4BG through a vessel, pipe or the like filled with an anion exchange resin. The eluted matter from the anion exchange resin is a polyamine. The polyamine is a general term for linear aliphatic hydrocarbons where two or more primary amino groups are connected, and in the present invention, this is a polymer containing two or more, preferably from 3 to 20, constituent units derived from a compound where any one or more of $R^1$ to $R^3$ in the nitrogen-containing compound represented by formula (1) is an alkyl group.

In the present invention, the amine that exists when heating the crude 1,4BG at 80° C. is preferably a primary or secondary amine-based compound having at least one N—H bond among the amine-based compounds of formula (1), or an eluted matter from an anion exchange resin containing primary polyamines having an N—H bond, and it is more preferred that both are present. Specifically, for example, in view of accelerating the decomposition of 2-(4-hydroxybutoxy)-tetrahydrofuran, a polymer containing from 2 to 20 constituent units derived from ethyleneamine eluted from an anion exchange resin having a polyethylenediamine, a primary amine such as octylamine, nonylamine, 1-aminodecane, aniline and phenethylamine, a secondary amine such as dipentylamine, dihexylamine, diheptylamine, dicyclohexylamine and N-methylaniline, a diamine such as 1,3-propanediamine and N,N-dimethyl-1,6-hexanediamine, a 5-membered ring amine such as 2,3-dihydro-1H-indole, and a 6-membered ring amine such as 4-aminomethylpiperidine and 1,2,3,4-tetrahydroquinoline, are preferred.

As for the amine further containing an oxygen atom, from the standpoint that the boiling point temperature under atmospheric pressure is close to that of 1,4BG a chain aminoalcohol such as 4-aminobutanol and 2-aminobutanol, and a cyclic amine such as 2-ethylmorpholine, prolinol, 3-hydroxypiperidine, 4-hydroxypiperidine, tetrahydrofurfurylamine and 3-aminotetrahydropyrane, are preferred. Furthermore, in view of preferably using a compound having a boiling point of 160 to 260° C. under atmospheric pressure, 1-aminodecane, dihexylamine, prolinol, 3-hydroxypiperidine, 4-hydroxypiperidine, 4-aminobutanol, tetrahydrofurfurylamine and the like are more preferred.

In the present invention, the amount of the amine is, as the concentration in terms of nitrogen atom, from 1 ppm by weight to 1 wt %, preferably from 5 to 300 ppm by weight, more preferably from 9 to 150 ppm by weight, based on the crude 1,4BG As the amount of the amine used is larger, the effects of the present invention are higher, but if the amount is too large, the cost of the amine increases, whereas if the amount of the amine used is too much decreased, the effects of the present invention are reduced.

In the present invention, the pH of the crude 1,4BG is not particularly limited but is preferably 7 or more. As for the crude 1,4BG having a pH of 7 or more, one having a pH of 7 or more may be selected or acquired from those 1,4BG produced by the above-described known techniques, but in the case where the pH of the crude 1,4BG is less than 7, the pH can be adjusted to be 7 or more by mixing or contacting the crude 1,4BG with a base component.

The pH value is preferably 7 or more, more preferably from 7.1 to 12, still more preferably from 7.3 to 11. A larger pH provides for higher effects of the present invention but requires increasing the required amount of the amine, and a smaller value leads to reduction in the effects.

EXAMPLES

The present invention is described in greater detail below by referring to Examples, but the present invention is not limited to these Examples as long as the gist of the present invention is observed. In the following Examples, the analysis of water was performed using a Karl-Fischer method. The analysis of 2-(4-hydroxybutoxy)-tetrahydrofuran was performed by gas chromatography, and the concentration thereof was calculated from the area percentage. Incidentally, a value obtained by subtracting the water concentration from 100 wt % was calculated, and the remaining wt % portion was calculated from the area percentage of each component in the gas chromatography. As for the amount of the amine eluted into 1,4BG from an anion exchange resin, the sample was burned in an argon/oxygen atmosphere, and the combustion gas generated was subjected to calculation of the concentration in terms of nitrogen atom by means of a trace nitrogen analyzer (Model TN-10, manufactured by Mitsubishi Chemical Analytech Co., Ltd.) employing a combustion/reduced pressure chemiluminescence detection method. Also, the amount of the amine (the concentration in terms of nitrogen atom) in the case of adding an amine-based compound was calculated from the amount of the mixed amine-based compound itself.

Example 1

A 1-L glass-made flask was charged with 300 g of commercially available 1,4-butanediol (produced by Mitsubishi Chemical Corporation) and 30.0 g of a solid weakly basic anion exchange resin (registered trademark: Diaion, model: WA20) containing a compound having an N—H bond-containing polyethylenediamine skeleton, and the contents were stirred at 45° C. for 2 hours. After the stirring, the anion exchange resin was separated by filtration.

Subsequently, 0.3 g of the obtained solution was diluted with 9.7 g of commercially available 1,4-butanediol (produced by Mitsubishi Chemical Corporation), and 1.8 g of water was added thereto to obtain crude 1,4BG The concentration of 2-(4-hydroxybutoxy)-tetrahydrofuran in the crude 1,4BG was measured and found to be 2,545 ppm by weight. The water concentration was 21.3 wt %, the pH was 8.2, and the amount of the polyamine containing from 2 to 20 constituent units derived from ethyleneamine eluted from the anion exchange resin was 9 ppm by weight as the concentration in terms of nitrogen atom.

This crude 1,4BG was placed in a 100-mL stainless steel autoclave and after nitrogen purging, heated at 170° C. for 2 hours. Analysis of 1,4BG obtained after heating was performed, and as a result, the concentration of 2-(4-hydroxybutoxy)-tetrahydrofuran was 1,950 ppm by weight. The results are shown in Table 1.

Example 2

The production was performed entirely in the same manner as in Example 1 except that 1.7 g of the obtained solution was diluted with 8.3 g of commercially available 1,4-butanediol (produced by Mitsubishi Chemical Corporation) and 2.3 g of water was added thereto to obtain crude 1,4BG. The concentration of 2-(4-hydroxybutoxy)-tetrahydrofuran in the crude 1,4BG was 2,374 ppm by weight, the water concentration was 24.7 wt %, the pH was 9.2, and the amount of the amine was 50 ppm by weight as the concentration in terms of nitrogen atom.

Analysis of 1,4BG obtained after heating was performed, and as a result, the concentration of 2-(4-hydroxybutoxy)-tetrahydrofuran was 1,751 ppm by weight. The results are shown in Table 1.

Example 3

A 100-mL glass-made flask was charged with 40 g of commercially available 1,4-butanediol (produced by Mitsubishi Chemical Corporation) and 4.0 g of a solid weakly basic anion exchange resin (registered trademark: Diaion, model: WA20) containing a compound having an N—H bond-containing polyethylenediamine skeleton, and the contents were stirred at room temperature for 2 hours. After the stirring, the anion exchange resin was separated by filtration. Subsequently, 1.8 g of water was added to 10 g of the obtained solution to obtain crude 1,4BG. The concentration of 2-(4-hydroxybutoxy)-tetrahydrofuran in the crude 1,4BG was measured and found to be 2,315 ppm by weight. The water concentration was 21.5 wt %, the pH was 9.1, and the amount of the polyamine containing from 2 to 20 constituent units derived from ethyleneamine eluted from the anion exchange resin was 110 ppm by weight as the concentration in terms of nitrogen atom.

This crude 1,4BG was placed in a 100-mL stainless steel autoclave and after nitrogen purging, heated at 170° C. for 2 hours. Analysis of 1,4BG obtained after heating was performed, and as a result, the concentration of 2-(4-hydroxybutoxy)-tetrahydrofuran was 1,998 ppm by weight. The results are shown in Table 1.

Example 4

The production was performed entirely in the same manner as in Example 1 except that 10.0 g of the obtained solution was not diluted with commercially available 1,4-butanediol (produced by Mitsubishi Chemical Corporation) but 1.4 g of water was added thereto to obtain crude 1,4BG The concentration of 2-(4-hydroxybutoxy)-tetrahydrofuran in the crude 1,4BG was 1,977 ppm by weight, the water concentration was 24.7 wt %, the pH was 9.5, and the amount of the amine was 300 ppm by weight as the concentration in terms of nitrogen atom.

Analysis of 1,4BG obtained after heating was performed, and as a result, the concentration of 2-(4-hydroxybutoxy)-tetrahydrofuran was 1,266 ppm by weight. The results are shown in Table 1.

Example 5

The production was performed entirely in the same manner as in Example 1 except that 5.0 g of the obtained solution was diluted with 5.0 g of commercially available 1,4-butanediol (produced by Mitsubishi Chemical Corporation) to obtain crude 1,4BG. The concentration of 2-(4-hydroxybutoxy)-tetrahydrofuran in the crude 1,4BG was 3,159 ppm by weight, the water concentration was 4.8 wt %, the pH was 9.2, and the amount of the amine was 150 ppm by weight as the concentration in terms of nitrogen atom.

Analysis of 1,4BG obtained after heating was performed, and as a result, the concentration of 2-(4-hydroxybutoxy)-tetrahydrofuran was 3,052 ppm by weight. The results are shown in Table 1.

Example 6

The production was performed entirely in the same manner as in Example 1 except that 5.0 g of the obtained solution was diluted with 5.0 g of commercially available 1,4-butanediol (produced by Mitsubishi Chemical Corporation) and 0.4 g of water was added thereto to obtain crude 1,4BG The concentration of 2-(4-hydroxybutoxy)-tetrahydrofuran in the crude 1,4BG was 3,069 ppm by weight, the water concentration was 10.4 wt %, the pH was 9.2, and the amount of the amine was 150 ppm by weight as the concentration in terms of nitrogen atom.

Analysis of 1,4BG obtained after heating was performed, and as a result, the concentration of 2-(4-hydroxybutoxy)-tetrahydrofuran was 2,606 ppm by weight. The results are shown in Table 1.

Example 7

The production was performed entirely in the same manner as in Example 1 except that 5.0 g of the obtained solution was diluted with 5.0 g of commercially available 1,4-butanediol (produced by Mitsubishi Chemical Corporation) and 1.0 g of water was added thereto to obtain crude 1,4BG. The concentration of 2-(4-hydroxybutoxy)-tetrahydrofuran in the crude 1,4BG was 3,198 ppm by weight, the water concentration was 14.4 wt %, the pH was 9.3, and the amount of the amine was 150 ppm by weight as the concentration in terms of nitrogen atom.

Analysis of 1,4BG obtained after heating was performed, and as a result, the concentration of 2-(4-hydroxybutoxy)-tetrahydrofuran was 2,485 ppm by weight. The results are shown in Table 1.

Example 8

The production was performed entirely in the same manner as in Example 3 except that commercially available 1,4BG was not put into contact with the anion exchange resin but N,N-dimethyl-1,3-propanediamine (9.0 mg) was added to commercially available 1,4BG The concentration of 2-(4-hydroxybutoxy)-tetrahydrofuran in the crude 1,4BG was 2,315 ppm by weight, the water concentration was 21.5 wt %, the pH was 10.8, and the amount of the amine was 175 ppm by weight as the concentration in terms of nitrogen atom.

Analysis of 1,4BG obtained after heating was performed, and as a result, the concentration of 2-(4-hydroxybutoxy)-tetrahydrofuran was 1,805 ppm by weight. The results are shown in Table 1.

Example 9

The production was performed entirely in the same manner as in Example 3 except that commercially available 1,4BG was not put into contact with the anion exchange resin but D,L-prolinol (9.0 mg) was added to commercially available 1,4BG. The concentration of 2-(4-hydroxybutoxy)-tetrahydrofuran in the crude 1,4BG was 2,315 ppm by weight, the water concentration was 21.5 wt %, the pH was 10.7, and the amount of the amine was 96 ppm by weight as the concentration in terms of nitrogen atom.

Analysis of 1,4BG obtained after heating was performed, and as a result, the concentration of 2-(4-hydroxybutoxy)-tetrahydrofuran was reduced to 2,203 ppm by weight. The results are shown in Table 1.

Example 10

The production was performed entirely in the same manner as in Example 3 except that commercially available 1,4BG was not put into contact with the anion exchange resin but 4-amino-1-butanol (9.0 mg) was added to commercially available 1,4BG. The concentration of 2-(4-hydroxybutoxy)-tetrahydrofuran in the crude 1,4BG was 2,315 ppm by weight, the water concentration was 21.5 wt %, the pH was 10.8, and the amount of the amine was 94 ppm by weight as the concentration in terms of nitrogen atom.

Analysis of 1,4BG obtained after heating was performed, and as a result, the concentration of 2-(4-hydroxybutoxy)-tetrahydrofuran was reduced to 2,116 ppm by weight. The results are shown in Table 1.

Comparative Example 1

The production was performed entirely in the same manner as in Example 3 except that commercially available 1,4BG was not put into contact with the anion exchange resin. The amount of the amine in the crude 1,4BG was below the detection limit, the concentration of 2-(4-hydroxybutoxy)-tetrahydrofuran was 2,315 ppm by weight, the water concentration was 21.5 wt %, and the pH was 5.5. Analysis of 1,4BG obtained after heating was performed, and as a result, the concentration of 2-(4-hydroxybutoxy)-tetrahydrofuran was increased to 2,580 ppm by weight. The results are shown in Table 1.

Comparative Example 2

The production was performed entirely in the same manner as in Example 10 except that the amount of water added was changed to 50 mg. The concentration of 2-(4-hydroxybutoxy)-tetrahydrofuran in the crude 1,4BG was 3,098 ppm by weight, the water concentration was 0.5 wt %, the pH was 10.8, and the nitrogen atom concentration was 94 ppm by weight. Analysis of 1,4BG obtained after heating was performed, and as a result, the concentration of 2-(4-hydroxybutoxy)-tetrahydrofuran was increased to 3,453 ppm by weight. The results are shown in Table 1.

Comparative Example 3

The production was performed entirely in the same manner as in Example 3 except that water was not added. The concentration of 2-(4-hydroxybutoxy)-tetrahydrofuran in the crude 1,4BG was 2,315 ppm by weight, the water concentration was 0 wt %, the pH was 10.9, and the nitrogen atom concentration was 123 ppm by weight. Analysis of 1,4BG obtained after heating was performed, and as a result, the concentration of 2-(4-hydroxybutoxy)-tetrahydrofuran was increased to 3,140 ppm by weight. The results are shown in Table 1.

TABLE 1

| | Crude 1,4-Butanediol | | Amine | | | | Change*2 in Amount of 2-(4-Hydroxybutoxy)-tetrahydrofuran |
|---|---|---|---|---|---|---|---|
| | 2-(4-hydroxy-butoxy)-tetrahydrofuran [ppm by weight] | Water [wt %] | Name | Structure | Amount*1 [ppm by weight] | pH | Between Before and After Heating [ppm by weight] |
| Example 1 | 2545 | 21.3 | anion exchange resin (WA20) | — | 9 | 8.2 | −595 |
| Example 2 | 2374 | 24.7 | anion exchange resin (WA20) | — | 50 | 9.2 | −623 |
| Example 3 | 2315 | 21.5 | anion exchange resin (WA20) | — | 110 | 9.1 | −317 |
| Example 4 | 1977 | 24.7 | anion exchange resin (WA20) | — | 300 | 9.5 | −711 |
| Example 5 | 3159 | 4.8 | anion exchange resin (WA20) | — | 150 | 9.2 | −107 |
| Example 6 | 3069 | 10.4 | anion exchange resin (WA20) | — | 150 | 9.2 | −463 |
| Example 7 | 3198 | 14.4 | anion exchange resin (WA20) | — | 150 | 9.3 | −713 |
| Example 8 | 2315 | 21.5 | N,N'-dimethyl-1,3-propanediamine | (structure) | 175 | 10.8 | −510 |
| Example 9 | 2315 | 21.5 | D,L-prolinol | (structure) | 96 | 10.7 | −112 |
| Example 10 | 2315 | 21.5 | 4-amino-1-butanol | (structure) | 94 | 10.8 | −199 |
| Comparative Example 1 | 2315 | 21.5 | none | — | (below detection limit) | 5.5 | +265 |
| Comparative Example 2 | 3098 | 0.5 | 4-amino-1-butanol | (structure) | 94 | 10.8 | +355 |
| Comparative Example 3 | 2315 | 0 | anion exchange resin (WA20) | — | 110 | 10.9 | +825 |

*1: In terms of nitrogen atom.
*2: "−" is a decrease from before heating, "+" is an increase from before heating.

While the invention has been described in detail and with reference to specific embodiments thereof, it will be apparent to one skilled in the art that various changes and modifications can be made therein without departing from the spirit and scope thereof. This application is based on a Japanese patent application filed on Jul. 4, 2011 (Application No. 2011-148328), the content thereof being incorporated herein by reference.

The invention claimed is:

1. A method for producing 1,4-butanediol, the method comprising heating a crude 1,4-butanediol containing from 0.01 to 0.5 wt % of 2-(4-hydroxybutoxy)-tetrahydrofuran and from 2 to 25 wt % of water at 80° C. or more in the presence of an amine to obtain a purified 1,4-butanediol.

2. A method for producing 1,4-butanediol, the method comprising heating a crude 1,4-butanediol containing from 0.01 to 0.5 wt % of 2-(4-hydroxybutoxy)-tetrahydrofuran at 80° C. or more in the presence of an amine and water in an amount of 2 to 25 wt % based on the crude 1,4-butanediol to obtain a purified 1,4-butanediol.

3. The method according to claim 1, wherein pH of the crude 1,4-butanediol is 7 or more.

4. The method according to claim 1, wherein an amount of the amine is from 1 ppm by weight to 1 wt % based on the crude 1,4-butanediol.

5. The method according to claim 1, wherein the crude 1,4-butanediol is heated at 80° C. or more in a distillation column.

6. The method according to claim 1, further comprising distilling the purified 1,4-butanediol.

7. The method according to claim 2, wherein pH of the crude 1,4-butanediol is 7 or more.

8. The method according to claim 2, wherein an amount of the amine is from 1 ppm by weight to 1 wt % based on the crude 1,4-butanediol.

9. The method according to claim 2, wherein the crude 1,4-butanediol is heated at 80° C. or more in a distillation column.

10. The method according to claim 2, further comprising distilling the purified 1,4-butanediol.

11. The method of claim 1, wherein the amount of water ranges from 7 to 25 wt %.

12. The method of claim 2, wherein the amount of water ranges from 7 to 25 wt %.

13. The method of claim 1, wherein the amine comprises a compound of formula (1):

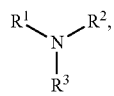

wherein:
each of $R^1$ to $R^3$ is independently a hydrogen atom, an alkyl group, an aryl group or an amino group; and
each of $R^1$ to $R^3$ may optionally have a substituent,
with the proviso that a case where all of $R^1$ to $R^3$ are a hydrogen atom is excluded.

14. The method of claim 2, wherein the amine comprises a compound of formula (1):

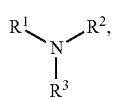

wherein:
each of $R^1$ to $R^3$ is independently a hydrogen atom, an alkyl group, an aryl group or an amino group; and
each of $R^1$ to $R^3$ may optionally have a substituent,
with the proviso that a case where all of $R^1$ to $R^3$ are a hydrogen atom is excluded.

15. The method of claim 1, wherein the amine compound comprises an anion exchange resin.

16. The method of claim 2, wherein the amine compound comprises an anion exchange resin.

* * * * *

UNITED STATES PATENT AND TRADEMARK OFFICE
CERTIFICATE OF CORRECTION

Page 1 of 2

PATENT NO. : 10,144,687 B2
APPLICATION NO. : 14/147885
DATED : December 4, 2018
INVENTOR(S) : Yusuke Izawa et al.

It is certified that error appears in the above-identified patent and that said Letters Patent is hereby corrected as shown below:

In the Claims

Column 13, Claim 13, Line 10:

"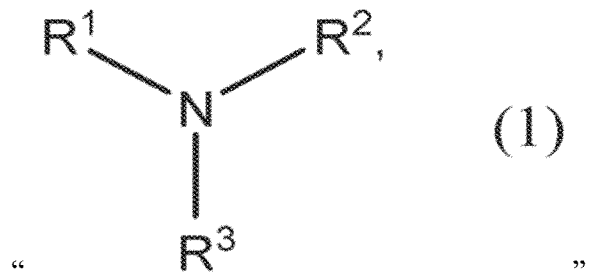"

Should read:

--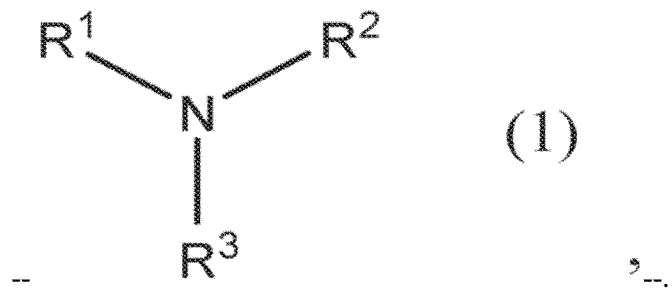--.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,144,687 B2

Column 14, Claim 14, Line 5:

"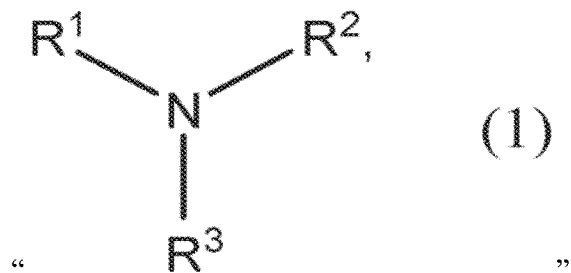"

Should read:

--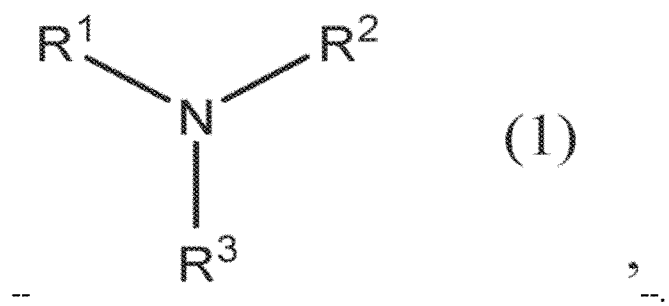,--.